United States Patent
Hama

(10) Patent No.: US 10,740,935 B2
(45) Date of Patent: Aug. 11, 2020

(54) MOLECULAR STRUCTURE GENERATION WITH SUBSTRUCTURE REPRESENTATIONS

(71) Applicant: International Business Machines Corporation, Armonk, NY (US)

(72) Inventor: Toshiyuki Hama, Setagaya (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 28 days.

(21) Appl. No.: 16/246,018

(22) Filed: Jan. 11, 2019

(65) Prior Publication Data

US 2020/0226804 A1 Jul. 16, 2020

(51) Int. Cl.
*G06T 11/20* (2006.01)
*G06F 16/901* (2019.01)
*G16C 20/90* (2019.01)
*G16C 20/80* (2019.01)

(52) U.S. Cl.
CPC ........ *G06T 11/206* (2013.01); *G06F 16/9024* (2019.01); *G16C 20/80* (2019.02); *G16C 20/90* (2019.02)

(58) Field of Classification Search
None
See application file for complete search history.

(56) References Cited

U.S. PATENT DOCUMENTS

| | | | | |
|---|---|---|---|---|
| 6,154,736 A * | 11/2000 | Chickering | ............ | G06N 7/005 706/59 |
| 2003/0225743 A1 * | 12/2003 | Inokuchi | ............. | G06F 16/9024 |
| 2007/0212719 A1 * | 9/2007 | Hlavacek | ................. | G16B 5/00 435/6.14 |
| 2008/0177478 A1 * | 7/2008 | Hlavacek | ............... | G16C 20/30 702/19 |
| 2010/0325141 A1 * | 12/2010 | Kunert | ................... | G16B 35/00 707/769 |
| 2011/0078189 A1 * | 3/2011 | Bonchi | ................. | G06Q 10/10 707/776 |
| 2013/0254169 A1 | 9/2013 | Barber | | |

(Continued)

OTHER PUBLICATIONS

Arvind et al., "Isomorphism and Canonization of Tournaments and Hypertournaments," Journal of Computer and System Sciences, 2010, vol. 76, pp. 509-523, Elsevier, 15 pages.

(Continued)

*Primary Examiner* — David H Chu
(74) *Attorney, Agent, or Firm* — Amin, Turocy & Watson, LLP

(57) ABSTRACT

Molecular structure generation with substructure representations is provided. The computer-implemented method, comprises: selecting, by a device operatively coupled to a processor, a vertex in an existing graph of a molecular structure; replacing, by the device, the selected vertex with a sub-structure representation of a molecule, the sub-structure representation including two or more vertices; connecting, by the device, a new vertex to the sub-structure representation in the existing graph to generate a new graph; labeling, by the device, each of a plurality of vertices of the new graph by a canonical labeling method; and determining, by the device, whether a vertex that has a minimum label is the new vertex.

25 Claims, 11 Drawing Sheets

(56) References Cited

U.S. PATENT DOCUMENTS

2015/0199593 A1* 7/2015 Kitamura ............. G06K 9/6267
                                                    382/180
2016/0357799 A1* 12/2016 Choi ................... G06F 16/2453
2019/0355444 A1* 11/2019 Yoo ......................... G06F 30/00

OTHER PUBLICATIONS

Peironcely et al., "OMG: Open Molecule Generator," Journal of Cheminformatics, Sep. 2012, ResearchGate, 14 pages.
McKay, "Isomorph-Free Exhaustive Generation," Journal of Algorithms, 1998, pp. 306-324, vol. 26, 19 pages.
Hartke et al., "McKay's Canonical Graph Labeling Algorithm," Communicating Mathematics, 2009, pp. 99-111, vol. 479, American Mathematical Society, 13 pages.

* cited by examiner

Graph 1

Orbit:{{A},{B, C, D}}
Label: [3(A), 2(B), 1(C), 0(D)]

Graph 1-2

Orbit:{{A},{B, C, D}, {E}}
Label: [4(A), 3(B), 2(C), 1(D), 0(E)]

Graph 1-1

Orbit:{{A},{B, C, D, E}}
Label: [4(A), 3(B), 2(C), 1(D), 0(E)]

Graph 1-1-1

Orbit:{{A},{B}, {C, D, E},{F}}
Label: [5(A), 4(B), 3(C), 2(D), 1(E), 0(F)]

Graph 1-2-1

Orbit:{{A},{B}, {C, D, F},{E}}
Label: [5(A), 4(B), 3(C), 2(D), 0(E), 1(F)]

Graph 1-2-2

Orbit:{{A}, {B}, {C, D}, {E, F}}
Label: [5(A), 4(B), 3(C), 2(D), 1(E), 0(F)]

Graph 1-2-3

Orbit:{{A},{B, C}, {D}, {E, F}}
Label: [5(A), 4(B), 3(C), 2(D), 1(E), 0(F)]

Graph 1-2-4

Orbit:{{A}, {B}, {C, D}, {E}, {F}}
Label: [5(A), 4(B), 3(C), 2(D), 1(E), 0(F)]

Graph 1

Graph 1'

Graph 1-2'

MOLECULAR STRUCTURE GENERATION WITH SUBSTRUCTURE REPRESENTATIONS

BACKGROUND

One or more embodiments relates to molecular structure generation with substructure representations.

SUMMARY

Molecular generation is an important tool for generating molecular structures that satisfy given specifications, such as the number of heavy atoms, the number of rings, etc. However, generation of molecular structures can require a large amount of computational resources and time, especially when generating huge molecular structures.

According to an aspect of the present invention, provided is a computer-implemented method comprising: selecting, by a device operatively coupled to a processor, a vertex in an existing graph of a molecular structure; replacing, by the device, the selected vertex with a sub-structure representation of a molecule, the sub-structure representation including two or more vertices; connecting, by the device, a new vertex to the sub-structure representation in the existing graph to generate a new graph; labeling, by the device, each of a plurality of vertices of the new graph by a canonical labeling method; and determining, by the device, whether a vertex that has a minimum label is the new vertex. According to this aspect, the number of vertices in the molecular structure is reduced, and thus the computational resources and time needed for the generation of the molecular structure is also saved. In addition, according to this aspect, redundant molecular structures are not generated and thus the computational resources and time needed for the generation of the molecular structure is further saved.

According to an aspect of the present invention, provided is the method of the preceding aspect, wherein the canonical labeling method includes isomorphic-free exhaustive generation. According to this aspect, redundant molecular structures are not generated and then the computational resources and time needed for the generation of the molecular structure is further saved.

According to an aspect of the present invention, provided is the method of the preceding aspect, wherein automorphisms of the labeling comprises a permutation group. The method further comprises: before selecting the vertex in the existing graph, generating an orbit of the permutation group including equivalent vertices in the existing graph in terms of labeling, wherein the selecting the vertex in the existing graph includes selecting a single vertex among two or more equivalent vertices in the orbit for each group. According to this aspect, a size of construction path for generating molecular structures is minimized and thus the computational resources and time needed for the generation of the molecular structure is further saved.

The foregoing aspect may also include an apparatus configured to perform the computer-implemented method, and a computer program product storing instructions embodied on a computer-readable medium or programmable circuitry, that, when executed by a processor or the programmable circuitry, cause the processor or the programmable circuitry to perform the computer-implemented method. The summary clause does not necessarily describe all features of the embodiments of the present invention. Embodiments of the present invention may also include sub-combinations of the features described above.

DETAILED DESCRIPTION

Hereinafter, example embodiments of the present invention will be described. The example embodiments shall not limit the invention according to the claims, and the combinations of the features described in the embodiments are not necessarily essential to the invention.

Figure 1A:
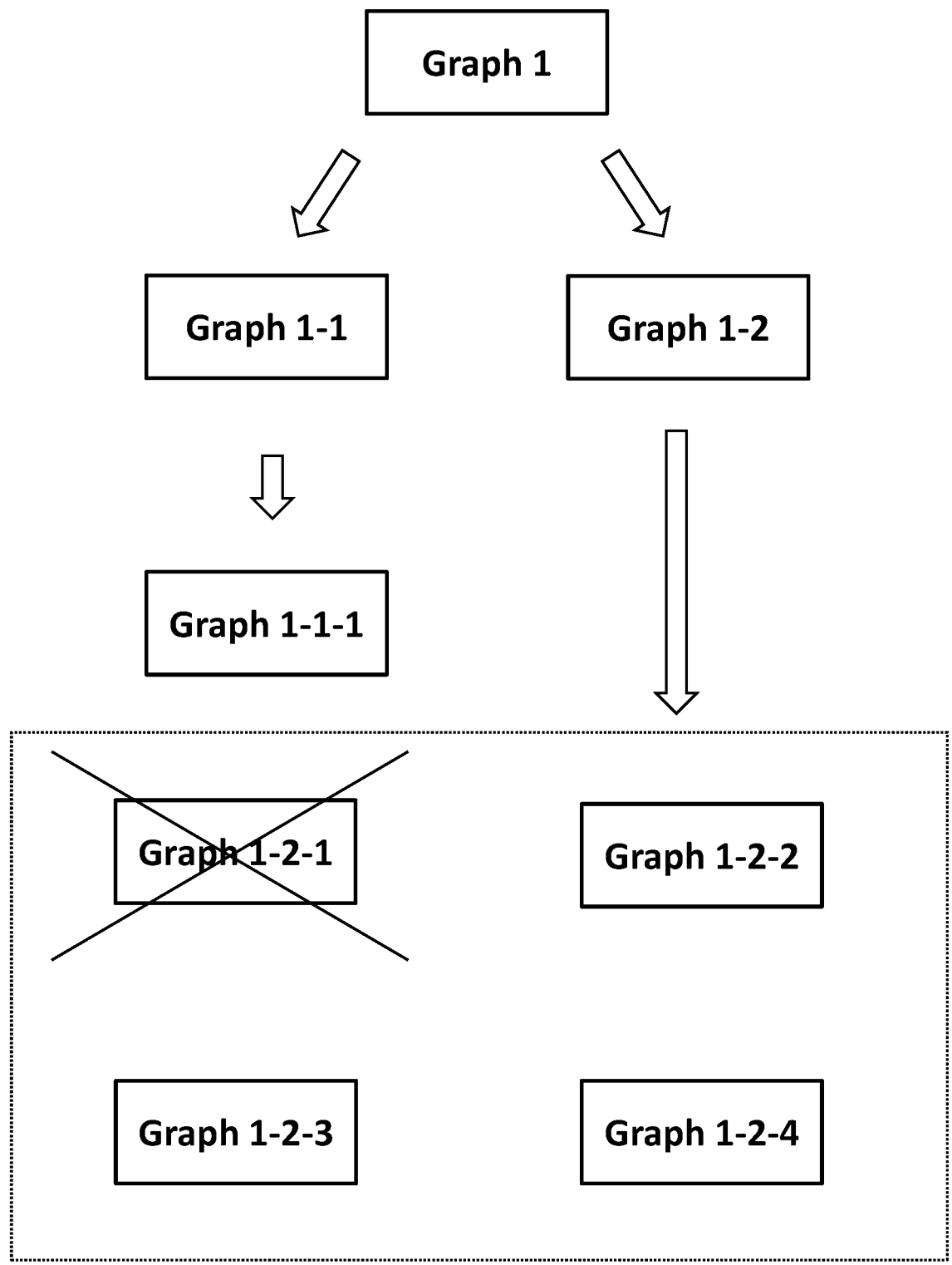
FIGS. 1A-C show a development of graphs according to an embodiment of the present invention.
Figure 1B:
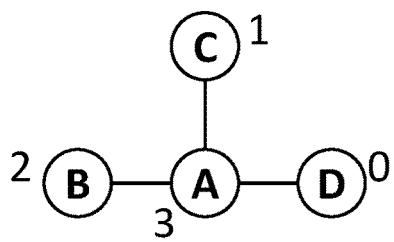
Figure 1B:
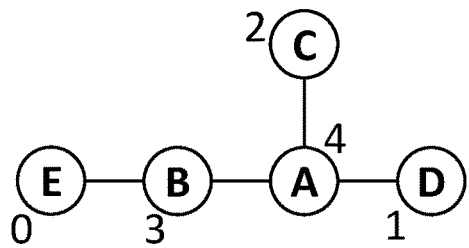
Figure 1B:
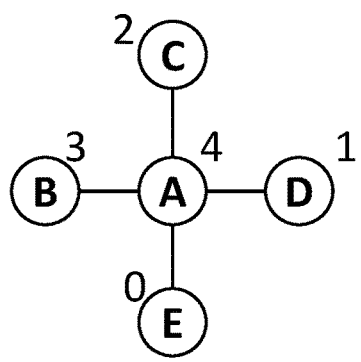
Figure 1B:
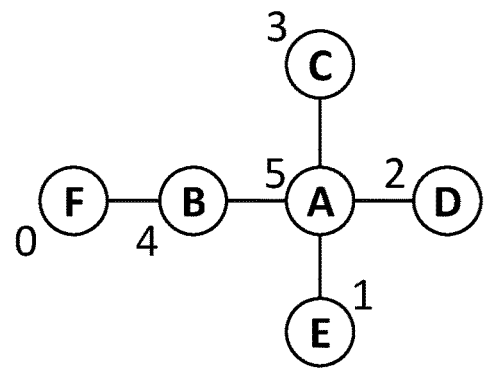
Figure 1C:
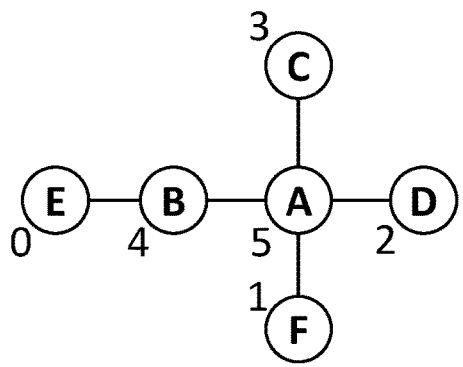
Figure 1C:
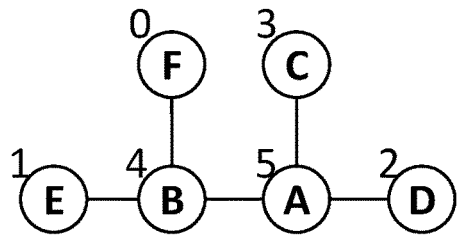
Figure 1C:
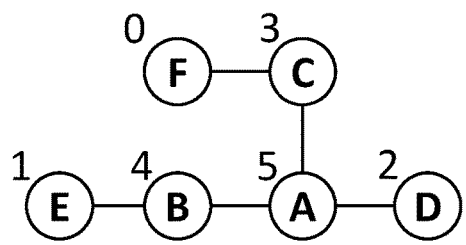
Figure 1C:
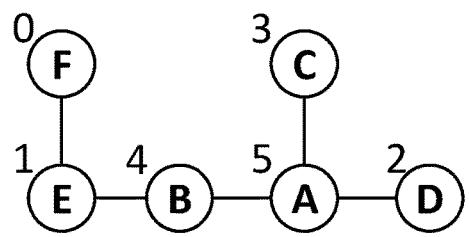
Figure 2:
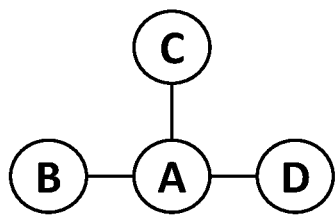
FIG. 2 shows a replacement of a vertex according to an embodiment of the present invention.
Figure 2:
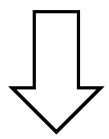
Figure 2:
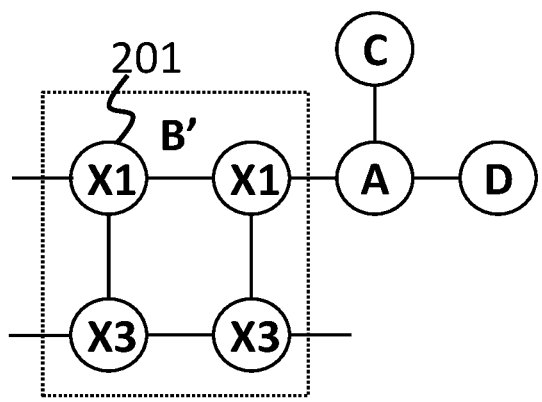
Figure 2:
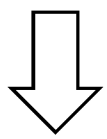
Figure 2:
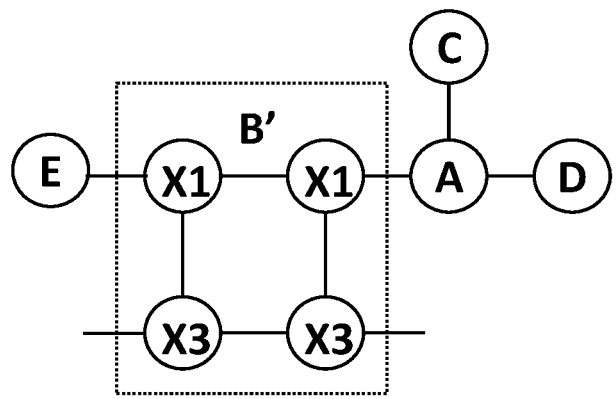

Here, a framework of embodiments of the present invention is explained in relation to FIGS. 1-2. FIG. 1A shows a development of graphs according to an embodiment of the present invention. In the framework, molecular structures are generated as graphs shown as Graph 1, Graph 1-1, Graph 1-2, Graph 1-1-1, Graph 1-2-2, Graph 1-2-3, and Graph 1-2-4. Structures of Graph 1, Graph 1-1, Graph 1-2, Graph 1-1-1, Graph 1-2-2, Graph 1-2-3, and Graph 1-2-4 are described in FIGS. 1B-1C. For example, the molecule structure of Graph 1 in FIG. 1 is shown in FIG. 1B.

In an explanation relating to FIGS. 1-2, a molecular generator generates molecular structures represented as Graph 1-1-1, Graph 1-2-2, Graph 1-2-3, and Graph 1-2-4 starting from a molecular structure of Graph 1.

As shown in FIG. 1B, Graph 1 includes 4 vertices shown as A, B, C, and D. Each vertex represents at least a part of a molecular structure (e.g., an atom, and/or sub-structure of a molecule). Each vertex may connect a determined number (e.g., 4, such as a carbon atom) of other vertices. Possible connections of each vertex with other vertices may be referred to as free hands. For example, the vertex A may have 4 free hands and 3 of them are used for the connections with other vertices in Graph 1.

An orbit of Graph 1 is represented as {{A}, {B, C, D}} by the group theory. This means that vertices B, C and D are equivalent. Graph 1 is labelled as [3, 2, 1, 0] where 3 corresponds to the vertex A, 2 corresponds to B, 1 corresponds to C, and 0 corresponds to D, by a canonical labeling method such as isomorphic-free exhaustive generation.

Since the vertices B, C, and D are equivalent in Graph 1, the molecular generator can select one vertex among the vertices B-D, (for example the vertex B) as an extending vertex, and extend the vertex B by connecting a new vertex E to the vertex B to generate Graph 1-2. The molecular generator can extend the vertex A by connecting a new vertex E to the vertex A to generate graph 1-1.

Graph 1-1 includes 5 vertices shown as A, B, C, D and E. An orbit of Graph 1-1 is represented as {{A}, {B, C, D, E}} by the group theory. This means that vertices B, C, D and E are equivalent. Graph 1-1 is labelled as [4, 3, 2, 1, 0] where 4 corresponds to the vertex A, 3 corresponds to B, 2 corresponds to C, 1 corresponds to D and 0 corresponds to E, by the canonical labeling method.

Graph 1-2 includes 5 vertices shown as A, B, C, D and E. An orbit of Graph 1 is represented as {{A}, {B}, {C, D}, E}} by the group theory. This means that vertices C and D are equivalent. Graph 1-2 is labelled as [4, 3, 2, 1, 0] where 4 corresponds to the vertex A, 3 corresponds to B, 2 corresponds to C, 1 corresponds to D and 0 corresponds to E, by the canonical labeling method.

In Graph 1-1, since the vertex A already has 4 connections with other vertices and cannot connect to an additional vertex, the molecular generator can select an extending vertex among the vertices B-E. Since the vertices B, C, D, and E are equivalent in Graph 1-1, the molecular generator can select one vertex among the vertices B-E, (for example the vertex B), and extend the vertex B by connecting a new vertex F to the vertex B to generate Graph 1-1-1.

In Graph 1-2, the molecular generator can select an extending vertex among the vertices A-E. The molecular generator can extend the vertex A by connecting a new vertex F to the vertex A of Graph 1-2 to generate Graph 1-2-1. The molecular generator can extend the vertex B by connecting a new vertex F to the vertex B of Graph 1-1 to generate Graph 1-2-2.

Since the vertices C, D are equivalent in Graph 1-2, the molecular generator can select one vertex among the vertices C and D, (for example the vertex C), and extend the vertex C by connecting a new vertex F to the vertex C of Graph 1-2 to generate Graph 1-2-3. The molecular generator can extend the vertex E by connecting a new vertex F to the vertex E of Graph 1-2 to generate Graph 1-2-4.

Here, Graph 1-2-1 is labelled as [5, 4, 3, 2, 0, 1] where 5 corresponds to the vertex A, 4 corresponds to B, 3 corresponds to C, 2 corresponds to D, 1 corresponds to E, and 0 corresponds to F by the canonical labeling method. According to the label of Graph 1-2-1, the new vertex F, which is the most recently added vertex, has the label of "1" but does not have the minimum label "0."

The molecular generator can further develop generated graphs such as Graph 1-1-1, Graph 1-2-1, Graph 1-2-2, Graph 1-2-3, Graph 1-2-3, and Graph 1-2-4 by further repeating an addition of a new vertex to the generated graphs. Meanwhile the molecular generator can abandon a graph in which a label of a new vertex is not the minimum label while developing graphs. For example, the molecular generator can abandon Graph 1-2-1.

The molecular generate may not further develop abandoned graphs such as Graph 1-2-1. Thereby the molecular generator can avoid generating a redundant graph such as Graph 1-2-1, which has the same structure as Graph 1-1-1. Therefore, the molecule generator can generate molecular structures with less computational resources and time.

FIG. 2 shows a replacement of a vertex, according to an embodiment of the present invention. In an embodiment, an extending vertex can be replaced with a sub-structure representation including two or more vertices before connecting a new vertex.

A vertex B of Graph 1 in FIG. 2, which is the same as Graph 1 of FIG. 1, is replaced with a sub-structure representation B', as shown in Graph 1'. The sub-structure representation B' includes two vertex X1s and two vertex X3s. The vertex X1 and vertex X3 can represent an atom. A new vertex E is connected to the vertex X1 of the sub-structure representation B, as shown in Graph 1-2'. The vertex X1 and vertex X3 can further be replaced with other sub-structure representations including a plurality of vertices.

According to the embodiment of FIG. 2, the sub-structure representation B' is represented by a single vertex B just before a new vertex E is introduced. Thereby, the molecular generator can treat a pending graph with a lower number of vertices.

Figure 3:
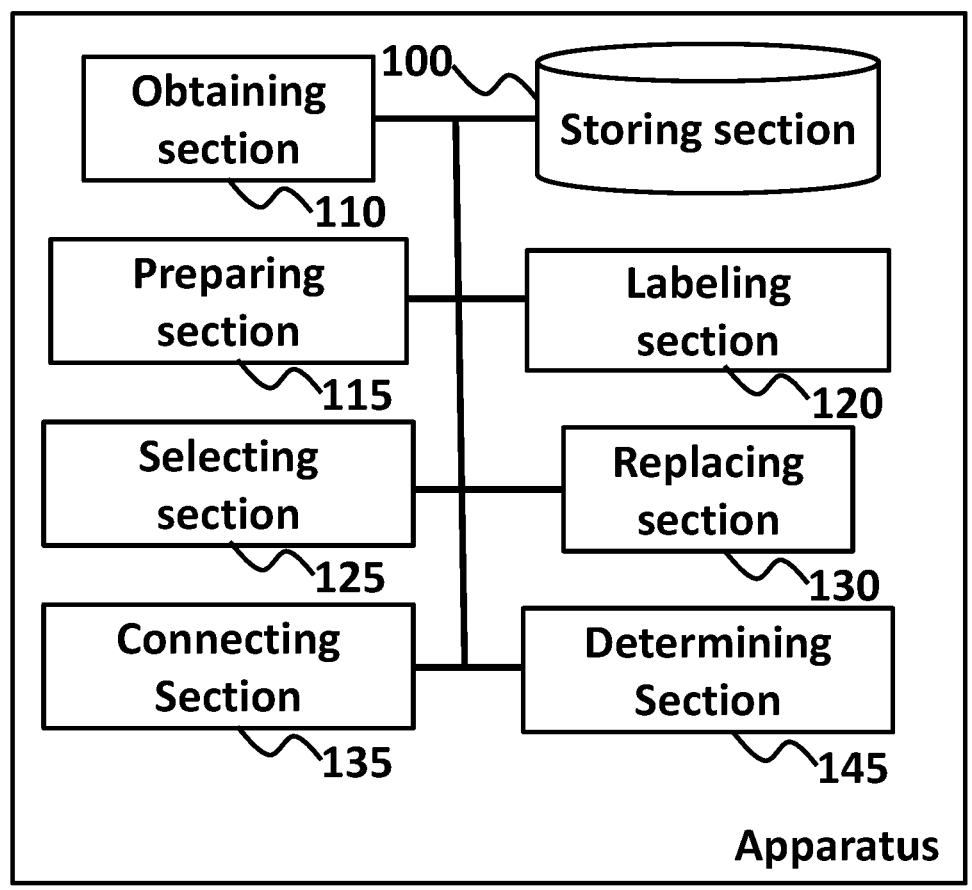
FIG. 3 shows an exemplary configuration of an apparatus according to an embodiment of the present invention.

FIG. 3 shows an exemplary configuration of an apparatus 10, according to an embodiment of the present invention. The apparatus 10 at least partially implements the framework described in FIGS. 1-2. Thereby, the apparatus 10 generates molecular structures with less computational resources and time.

The apparatus 10 can include a processor and/or programmable circuitry. The apparatus 10 can further include one or more computer readable mediums collectively including instructions. The instructions can be embodied on the computer readable medium and/or the programmable circuitry. The instructions, when executed by the processor or the programmable circuitry, can cause the processor or the programmable circuitry to operate as a plurality of operating sections.

Thereby, the apparatus 10 can be regarded as including a storing section 100, an obtaining section 110, a preparing section 115, a labeling section 120, a selecting section 125, a replacing section 130, a connecting section 135, and a determining section 145.

The storing section 100 stores information used for the processing that the apparatus 10 performs. The storing section 100 can also store a variety of data/instructions used for operations of the apparatus 10. One or more other elements in the apparatus 10 (e.g., the obtaining section 110, the preparing section 115, the labeling section 120, the selecting section 125, the replacing section 130, the connecting section 135, and the determining section 145) can communicate data directly or via the storing section 100, as necessary. In some embodiments, the apparatus 10 can be implemented by two or more computer devices.

The storing section 100 can be implemented by a volatile or non-volatile memory of the apparatus 10. In some embodiments, the storing section 100 stores molecular structures, graphs, sub-structure representations, determined requirements, an initial graph for generating molecular structures, and other data related thereto.

The obtaining section 110 obtains data used for operations of the apparatus 10. For example, the obtaining section 110 can obtain the sub-structure representations and/or the determined requirements.

The preparing section 115 prepares sub-structure representations of a molecule. In an embodiment, the sub-structure representation can represent a sub-structure of a molecule and can correspond to a building block used for the molecular generation. For example, the sub-structure representations can include aromatic rings (e.g., benzene, pyridine, naphthalene, etc.), alicyclic ring (e.g., cyclo butane, cyclohexane, etc), amino acids, and/or other functional groups.

The sub-structure representations can include an original representation, an isomorphic equivalent representation, and a single vertex representation. Details of the sub-structure representations are explained below.

The labeling section 120 performs a canonical labeling method, such as isomorphic-free exhaustive generation. Thereby, the labeling section 120 can label each of a plurality of vertices of a graph.

The labeling section 120 can also generate a plurality of groups of equivalent vertices from vertices in a graph by the canonical labeling method. In an embodiment, the labeling section 120 can generate an orbit of labeling to generate a plurality of groups of vertices. In the orbit, each group includes equivalent vertices in the existing graph.

The selecting section 125 selects a vertex in an existing graph of a molecular structure as an extending vertex in the existing graph. In an embodiment, the selecting section 125 can select a single vertex among two or more equivalent vertices for each group in the orbit. In an embodiment, the selecting section 125 can select, as the single vertex, a single vertex representation or a vertex that is not the single vertex representation.

The replacing section 130 replaces the vertex selected by the selecting section 125 with the sub-structure representation including two or more vertices. In an embodiment, the replacing section 130 can replace the single vertex representation with the original representation or the isomorphic equivalent representation. When the selecting section 125 has selected a vertex that is not a single vertex representation, the replacing section 130 can not replace the selected vertex with the sub-structure representation.

The connecting section 135 connects a new vertex to the vertex selected at S330 to generate a new graph. When the selected vertex is replaced with the sub-structure representation by the replacing section 130, the connecting section 135 can connect a new vertex to the sub-structure representation that is replaced from the selected vertex, in the existing graph to generate a new graph. The connecting section 135 can also provide an initial graph at a beginning of generation of molecular structures.

The determining section 145 determines whether a vertex that has a minimum label in the new graph is the new vertex. The determining section 145 can abandon the new graph in response to determining that the vertex that has the minimum label is not the new vertex. Thereby, the determining section 145 can avoid generating redundant graphs.

Figure 4:
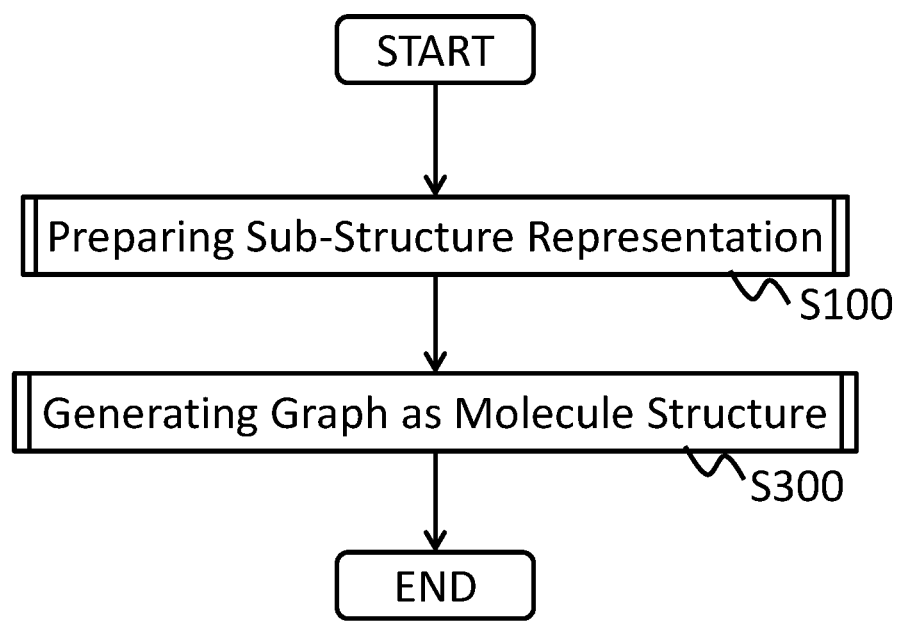
FIG. 4 shows an operational flow according to an embodiment of the present invention.

FIG. 4 shows an operational flow according to an embodiment of the present invention. The present embodiment describes an example in which an apparatus, such as the apparatus 10, performs operations from S100 to S300, as shown in FIG. 4.

At S100, a preparing section, such as the preparing section 115, prepares sub-structure representations of a molecule. In an embodiment, the preparing section can generate an isomorphic equivalent representation and a single vertex representation from a corresponding original representation. In another embodiment, the preparing section can receive a plurality of correspondences between the original representation, the isomorphic equivalent representation, and the single vertex representation.

Figure 5:
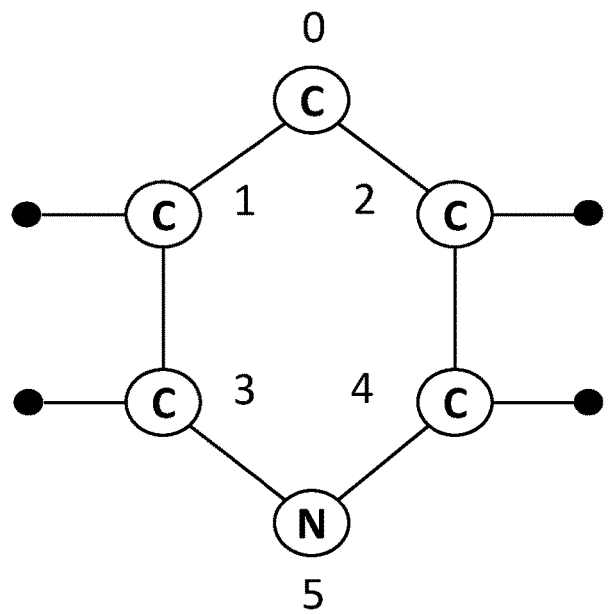
FIG. 5 shows an example of an original representation of according to an embodiment of the present invention.

FIG. 5 shows an example of an original representation according to an embodiment of the present invention. The original representation of FIG. 5 represents pyridine and includes six vertices. The six vertices correspond to five carbon (shown as "C" numbered "0"–"4") atoms and 1 nitrogen atom (shown as "N" numbered "5").

The original representation of FIG. 5 includes only four free hands although it includes five carbon atoms and a nitrogen atom. This means that at least some of the carbon atoms can be treated as not able to connect to other vertices (e.g., other atoms). In the embodiment of FIG. 5, the carbon atoms numbered "1"–"4" can connect to other vertices while the carbon atom numbered "0" and the nitrogen atom cannot connect to other vertices. In another embodiment, all vertices in the original representation can connect to other vertices.

Figure 6A:
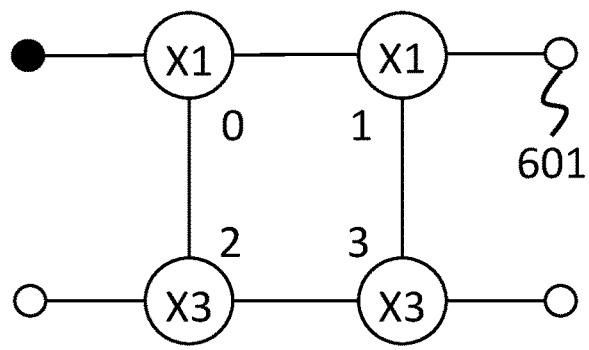
FIGS. 6A-B show an example of an isomorphic equivalent representation according to an embodiment of the present invention.
Figure 6B:
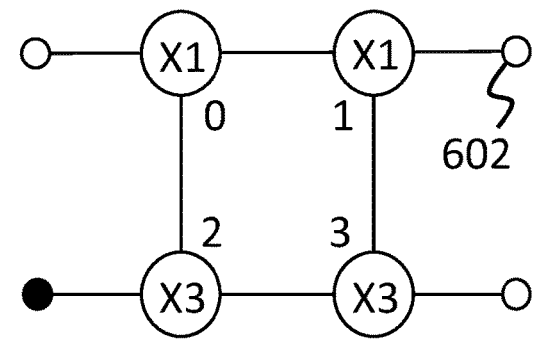

FIGS. 6A-B show an example of an isomorphic equivalent representation according to an embodiment of the present invention. The isomorphic equivalent representations of FIGS. 6A-B are isomorphically equivalent to the original representation of FIG. 5, and represent the original representation of FIG. 5. The isomorphic equivalent representations of FIGS. 6A-B include 4 vertices shown as two X1 and two X3.

The two X1 atoms correspond to the three carbon atoms numbered "0", "1" and "2" in the original representation of FIG. 5. The two X3 atoms correspond to the two carbon atoms numbered "3" and "4" and the nitrogen atom numbered "5" in the original representation of FIG. 5. A connection from the X1 atom numbered "0" in FIG. 6A corresponds to a connection from the carbon atom numbered "1" or "2" in FIG. 5. A connection from the X3 atom numbered "2" in FIG. 6B corresponds to a connection from the carbon atom numbered "3" or "4" in FIG. 5.

The isomorphic equivalent representation of FIG. 6A is distinguished from the isomorphic equivalent representation of FIG. 6B by a vertex at which the representation is connected to the existing graph. The isomorphic equivalent representation of FIG. 6A connects to the existing graph at the vertex X1 (which corresponds to the carbon atom numbered "1" or "2" in FIG. 5). The isomorphic equivalent representation of FIG. 6B connects to the existing graph at the vertex X3 (which corresponds to the carbon atom numbered "3" or "4" in FIG. 5).

Figure 7A:
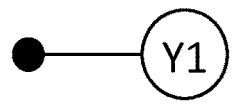
FIGS. 7A-B show an example of a single vertex representation according to an embodiment of the present invention.
Figure 7B:
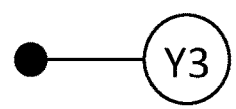

FIGS. 7A-B show an example of a single vertex representation according to an embodiment of the present invention. The single vertex representations of FIGS. 7A-B represent the original representation of FIG. 5. The single representation of FIGS. 7A-B includes a single vertex shown as Y1 and Y3.

In the embodiments explained in relation to FIGS. 5-7, the preparing section can prepare a correspondence between the original representation of FIG. 5 and the single representation of FIGS. 7A-B, and store the correspondence in a storing section, such as the storing section 100. Thereby, a replacing section, such as the replacing section 130, can later replace a selected single vertex with a corresponding original representation or isomorphic equivalent representation.

The preparing section can prepare a correspondence between the original representation of FIG. 5 and the isomorphic equivalent representations of FIG. 6A-B, and store the correspondence in the storing section. Thereby, the replacing section can later replace a selected single vertex with a corresponding isomorphic equivalent representation.

Figure 8:
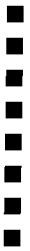
FIG. 8 shows an example of correspondences between representations according to an embodiment of the present invention.

FIG. 8 shows an example of correspondences between representations, according to an embodiment of the present invention. In an embodiment, the preparing section can store correspondences between the original representations, the isomorphic equivalent representations, and single vertex representations, such as those shown in FIG. 8, in a storing section, such as storing section 100.

Figure 9:
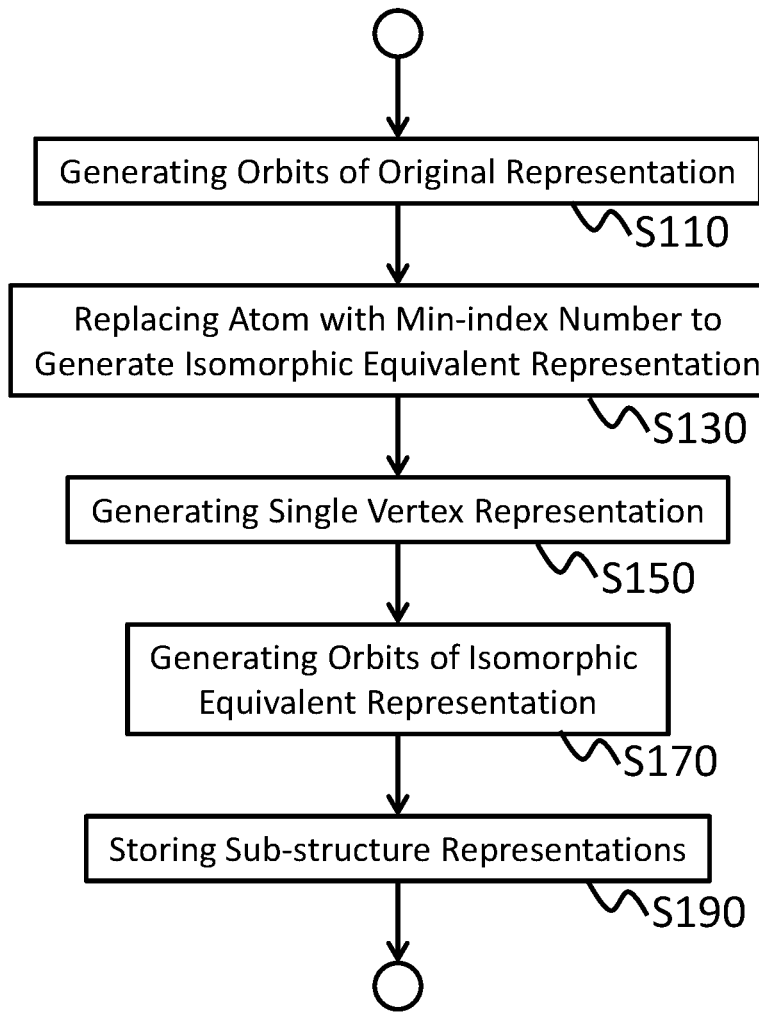
FIG. 9 shows a sub-flow of preparing a substructure representation in the flow of FIG. 4 according to an embodiment of the present invention.

FIG. 9 shows a sub-flow of S100 in the flow of FIG. 4 according to an embodiment of the present invention. An apparatus, such as the apparatus 100, can perform operations of S110-S190 of FIG. 9 at the operation S100 of FIG. 4.

At S110, a labeling section, such as the labeling section 120, generates a plurality of groups of equivalent vertices in an original representation. In an embodiment, the labeling section can perform a canonical labeling method, such as isomorphic-free exhaustive generation to the original representation for generating the plurality of groups of equivalent vertices.

For example, when the original representation is given by FIG. 5, a simplified molecular-input line-entry system (SMILES) notation of the original representation is X=C1 ([*])C([*])NC([*])C([*])C1. The labeling section can generate orbits: {{0}, {1, 2}, {3, 4}, {5}}. In the original representation of FIG. 5, C numbered "0" and N numbered "5" are preliminarily determined as not having any free hands.

At S130, a preparing section, such as the preparing section 115, replaces one or more atoms in the original representation with the SMILES name and min index number in the original representation, and can further eliminate vertices with no free hand from the original representation. For example, the preparing section can eliminate C numbered "0" and N numbered "5" from the original representation of FIG. 5, replace equivalent vertices C numbered "1" and C numbered "2" with the SMILES name "X"+min number "1" among them to generate two "X1" vertices, and replace equivalent vertices C numbered "3" and C numbered "4" with the SMILES name "X"+min number "3" among them to generate two "X3" vertices. Thereby, the preparing section can prepare the two isomorphic equivalent representations shown in FIGS. 6A-B.

At S150, the preparing section prepares single vertex representations corresponding to isomorphic equivalent representations generated at S130. For example, the preparing section can prepare two single vertex representations shown in FIGS. 7A-B corresponding to the two isomorphic equivalent representations shown in FIGS. 6A-B.

At S170, the labeling section generates a plurality of groups of equivalent vertices in the isomorphic equivalent representations generated at S130. The labeling section can generate the plurality of groups of equivalent vertices in the same manner as explained in relation to S110. For example, the labeling section can generate orbits: {{0}, {1}, {2}, {3} from the two isomorphic equivalent representations shown in FIGS. 6A-B.

Then, the preparing section can determine candidates of an extended vertex. In an embodiment, the preparing section can determine vertices that are not connected to the existing graph as the candidates of the extended vertex. For example, the preparing section can determine the X1 numbered "1", the two X3 vertices in FIG. 6A, as the candidates of the extended vertices, and determine the X3 numbered "3", the two X1 vertices in FIG. 6B, as the candidates of the extended vertices.

At S190, the preparing section stores correspondence between the original representation processed at S110, the isomorphic equivalent representations generated at S130, and the single vertex representations generated at S150. In an embodiment, the preparing section can store the correspondence, as shown in FIG. 8.

In embodiments relating to FIG. 9, the preparing section can prepare correspondences of one original representation. In other embodiments, the preparing section can prepare correspondences of two or more original representations.

Figure 10:
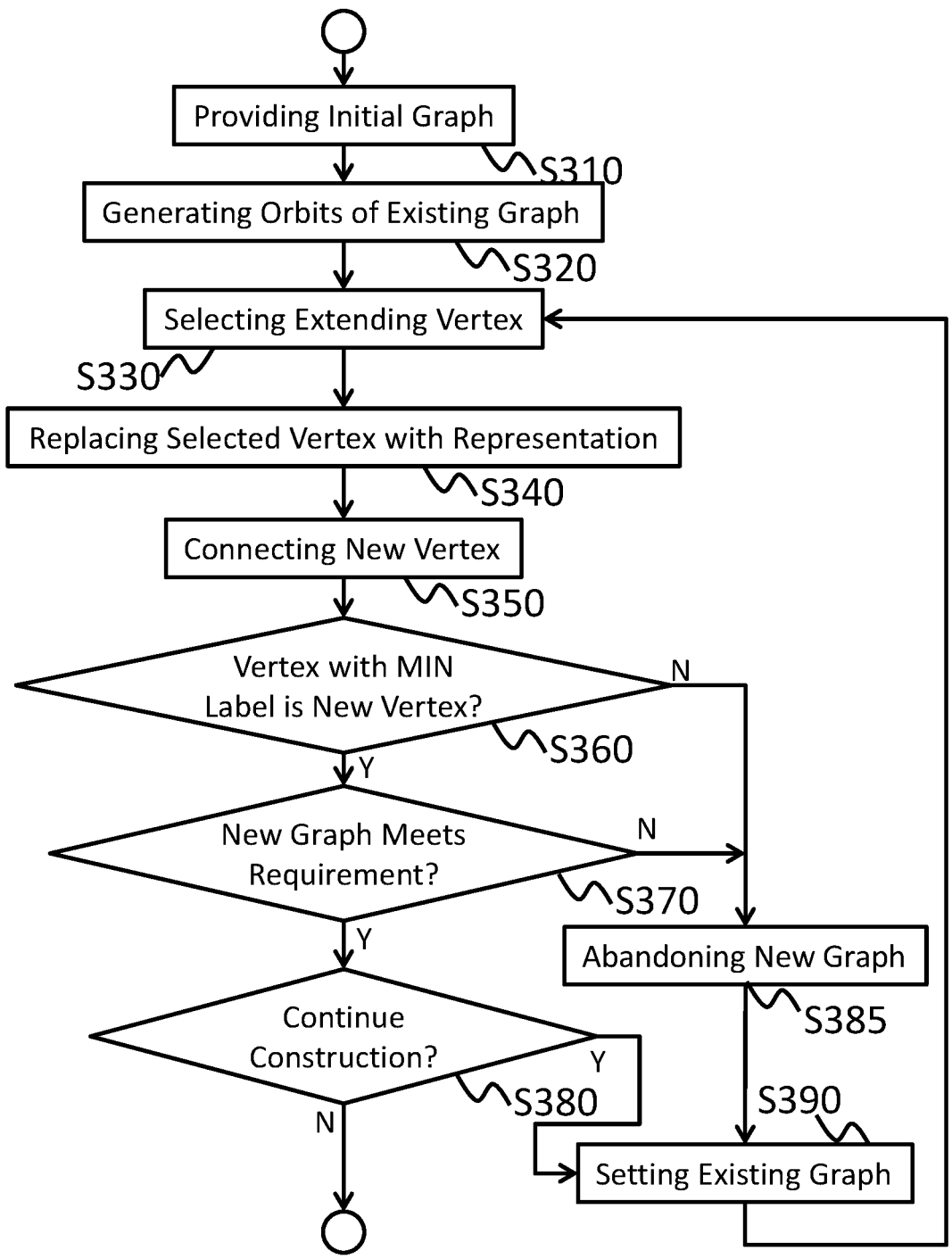
FIG. 10 shows a sub-flow of generating a graph as a molecule structure in the flow of FIG. 4 according to an embodiment of the present invention.

FIG. 10 shows a sub-flow of S300 in the flow of FIG. 4 according to an embodiment of the present invention. The apparatus performs operations of S310-S390 of FIG. 10 at the operation S300 of FIG. 4.

At S310, a connecting section, such as the connecting section 135, provides an initial graph. The initial graph can include one or two initial vertices. The initial graph can be preliminarily given by a user of the apparatus, and can be stored in a storing section, such as the storing section 100.

At S320, a labeling section, such as the labeling section 120, generates a plurality of groups of equivalent vertices in an existing graph. In an embodiment, the labeling section can perform a canonical labeling method, such as isomorphic-free exhaustive generation, on the existing graph to generate the plurality of groups of equivalent vertices.

At S320, the existing graph is the initial graph provided at S310. In an embodiment, the labeling section can generate an orbit of the permutation groups of equivalent vertices in terms of labeling before selecting the vertex in the existing graph. For example, when the existing graph is Graph 1 in FIG. 1B, the labeling section can generate orbit: {{A}, {B, C, D} }. In an embodiment, the labeling section can generate the orbit according to a known labeling algorithm such as disclosed in S. G. Hartke and A. Radcliffe. "Mckay's canonical graph labeling algorithm", In Communicating Mathematics, 479, 99-111. American Mathematical Society, 2009.

At S330, a selecting section, such as the selecting section 125, selects a single vertex in the existing graph as an extended vertex. In an embodiment, the selecting section can select a single vertex among two or more equivalent vertices for each group in the orbit. In an embodiment, the selecting section can select a not-yet-selected vertex among vertices in the existing graph, while the selecting section can treat a vertex that is equivalent with the selected vertex as an already-selected vertex.

In an example where Graph 1 of FIG. 2 is the existing graph, the selecting section can select one vertex among vertices A-D (or vertices A-B) when none of the vertices are yet selected. The selecting section can select A when at least one of the vertices B-D has already been selected. The selecting section can select one of the vertices B-D when the vertex A has already been selected.

At S340, a replacing section, such as the replacing section 130, replaces the vertex selected at S330 with the sub-structure representation including two or more vertices. In an embodiment, the replacing section can replace the single vertex representation with the original representation or the isomorphic equivalent representation. If the selected vertex cannot be replaced (e.g., the selected vertex is not a single vertex representation), then the apparatus can proceed with an operation of S350.

In an example where Graph 1 of FIG. 2 is the existing graph and the vertex B is a selected single vertex representation, the replacing section can replace the vertex B with a sub-structure representation B' including two X1 vertices and two X3 vertices. Thereby, the replacing section can generate Graph 1' from Graph 1 in FIG. 2.

In an embodiment, the replacing section can first remove the selected vertex from the existing graph and connect the sub-structure representation of a molecule to a portion of a remaining graph. In the embodiment, the replacing section can connect the sub-structure representation at one of the two or more vertices in the sub-structure representation according to a type of the selected vertex, to the remaining graph. In an example, when the selected vertex is the single vertex representation shown as Y1 in FIG. 7A, the replacing section can connect the sub-structure representation of FIG.

6A to a portion of the existing graph except the selected vertex (such as a portion of Graph 1 except the selected vertex B in FIG. 2).

Here, the replacing section can connect the sub-structure representation at a vertex X1, not a vertex X3 in FIG. 6A in response to determining that the selected vertex is Y1, not Y3. Meanwhile, the replacing section can connect the sub-structure representation at a vertex X3, not a vertex X1 in FIG. 6B in response to determining that the selected vertex is Y3, not Y1. Thereby, the single vertex representations, such as shown in FIG. 7, can distinguish a location at which the sub-structure representation is connected to the existing graph.

At S350, a connecting section, such as the connecting section 135, connects a new vertex to the extended vertex of the existing graph. In an embodiment, the connecting section can connect a new vertex to the sub-structure representation that is replaced from the selected vertex at S340. In an example of FIG. 2, the connecting section can connect a new vertex E to the sub-structure representation B' in Graph 1' to generate new Graph 1-2'. Graph 1-2' can correspond to Graph 1-2 in FIG. 1B. In an embodiment, the connecting section can connect the new vertex to the extended vertex selected at S330 of the existing graph when the selected vertex is not a single vertex representation.

In an embodiment, the connecting section can connect the new vertex to the sub-structure representation at a vertex determined by a determined algorithm in the sub-structure representation. In the embodiment, the vertex connecting to the new vertex can be determined based on a corresponding single vertex representation. In an example of FIG. 2, in response to determining that the corresponding single vertex representation is Y1 (or Y3) in FIG. 7, the connecting section can connect the new vertex E to vertex 201 (X1) in the sub-structure representation B' in Graph 1' to generate Graph 1-2'.

In an embodiment, the new vertex connected at S350 can represent a sub-structure of a molecule. In the embodiment, the new vertex can be a single vertex representation, and can be replaced with the sub-structure representation of the molecule including two or more vertices upon further operations of FIG. 10. For example, the new vertex can be a single vertex representation representing a building block (e.g., benzene ring) for generating molecular structures.

At S360, a determining section, such as the determining section 145, can determine whether a vertex that has a minimum label is the new vertex. Thereby, the determining section can perform a canonical construction path check for generation of molecular structures.

At first, a labeling section such as the labeling section 120 can perform a canonical labeling method such as isomorphic-free exhaustive generation on the new graph. Thereby, the labeling section can label each of a plurality of vertices of the new graph generated at the latest iteration of S350, and can also generate a plurality of groups of equivalent vertices in the new graph. In an embodiment, the labeling section can perform the labeling in the same manner as explained in relation to the operation of S320.

Then, the determining section can determine whether a vertex that has a minimum label according to the canonical labeling method is the new vertex. In response to determining that the vertex that has the minimum label is the new vertex, the determining section proceeds with an operation of S370. In response to determining that the vertex that has the minimum label is not the new vertex, the determining section proceeds with an operation of S385.

At S370, the determining section determines whether the new graph meets a determined requirement of the molecular structures. The determined requirement can be a specification of target molecule structures. In an embodiment, the determined requirement can include at least one of a number of specific atoms, a number of specific fragments of molecular structures, molecular weight, etc. For example, the determining section can determine whether a number of benzene ring structures in the new graph are within a threshold.

In response to determining that the new graph meets the determined requirement, the determining section proceeds with an operation of S380. In response to determining that the new graph does not meet the predetermine requirement, the determining section proceeds with an operation of S385.

At S380, the determining section determines whether to continue construction of molecular structures based on determined criteria. In an embodiment, the determine section can determine to end the construction of molecular structures in response to determining that a determined number of molecular structures are generated, a determined time has passed, and/or it is not possible to further generate molecular structures.

In response to determining to continue construction of molecular structures, the determining section proceeds with an operation of S390. In response to determining to end construction of molecular structure, the determining section ends the operation of S300.

At S385, the determining section abandons the new graph. Thereby, the determining section abandons the new graph in response to determining that the vertex that has the minimum label is not the new vertex or in response to determining that the new graph does not meet the determined requirement.

At S390, the determining section sets an existing graph for the next iteration of S330-S390. In an embodiment, the determining section can set the existing graph based on a depth-first search or a width-first search in the construction path tree. For example, the determining section can set Graph 1-2' of FIG. 2 as an existing graph after generating Graph 1-2' as the new graph.

In another example, the determining section can set Graph 1 of FIG. 2 again as an existing graph after generating Graph 1-2' as the new graph. In the example, the determining section can select a vertex A as the extended vertex at a subsequent operation of S330, and can not select the vertex B nor vertices C-D, which are equivalent to the already selected vertex B.

In an embodiment, the determining section may not select, as a newly existing graph, graphs that have been abandoned at previous iterations of S385 and graphs that do not have vertices that have not yet been selected at S330. Thereby the apparatus can generate molecular structures without redundancy.

According to the operational flow of FIG. 4, the apparatus can efficiently exhaustively generate molecular structures according to the determined requirement with reduced redundancy. Since the apparatus uses sub-structure representations such as single vertex representation and isomorphic equivalent representation for describing molecular structure, the apparatus can reduce a number of vertices during the generation of molecular structures.

Thereby, the apparatus can save computational resources and time in generating molecular structures. In particular, the apparatus can reduce time and computational resource for the labeling process at S360.

Various embodiments of the present invention can be described with reference to flowcharts and block diagrams whose blocks can represent (1) steps of processes in which operations are performed or (2) sections of apparatuses responsible for performing operations. Certain steps and sections can be implemented by dedicated circuitry, programmable circuitry supplied with computer-readable instructions stored on computer-readable media, and/or processors supplied with computer-readable instructions stored on computer-readable media. Dedicated circuitry can include digital and/or analog hardware circuits and can include integrated circuits (IC) and/or discrete circuits. Programmable circuitry can include reconfigurable hardware circuits comprising logical AND, OR, XOR, NAND, NOR, and other logical operations, flip-flops, registers, memory elements, etc., such as field-programmable gate arrays (FPGA), programmable logic arrays (PLA), etc.

Figure 11:
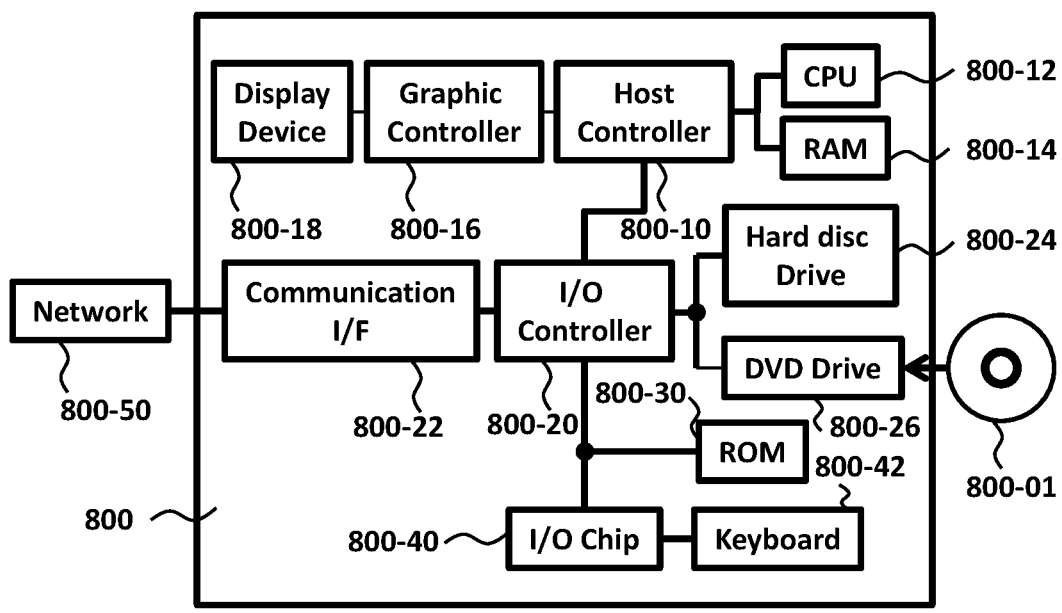
FIG. 11 shows an exemplary hardware configuration of a computer that functions as a system, according to an embodiment of the present invention.

FIG. 11 shows an exemplary hardware configuration of a computer configured for the embodiments of the present invention. A program that is installed in the computer 800 can cause the computer 800 to function as or perform operations associated with apparatuses of the embodiments of the present invention or one or more sections (including modules, components, elements, etc.) thereof, and/or cause the computer 800 to perform processes of the embodiments of the present invention or steps thereof. Such a program can be executed by the CPU 800-12 to cause the computer 800 to perform certain operations associated with some or all of the blocks of flowcharts and block diagrams described herein.

The computer 800 according to the present embodiment includes a CPU 800-12, a RAM 800-14, a graphics controller 800-16, and a display device 800-18, which are mutually connected by a host controller 800-10. The computer 800 also includes input/output units such as a communication interface 800-22, a hard disk drive 800-24, a DVD-ROM drive 800-26 and an IC card drive, which are connected to the host controller 800-10 via an input/output controller 800-20. The computer also includes legacy input/output units such as a ROM 800-30 and a keyboard 800-42, which are connected to the input/output controller 800-20 through an input/output chip 800-40.

The CPU 800-12 operates according to programs stored in the ROM 800-30 and the RAM 800-14, thereby controlling each unit. The graphics controller 800-16 obtains image data generated by the CPU 800-12 on a frame buffer or the like provided in the RAM 800-14 or in itself, and causes the image data to be displayed on the display device 800-18.

The communication interface 800-22 communicates with other electronic devices via a network 800-50. The hard disk drive 800-24 stores programs and data used by the CPU 800-12 within the computer 800. The DVD-ROM drive 800-26 reads the programs or the data from the DVD-ROM 800-01, and provides the hard disk drive 800-24 with the programs or the data via the RAM 800-14. The IC card drive reads programs and data from an IC card, and/or writes programs and data into the IC card.

The ROM 800-30 stores therein a boot program or the like executed by the computer 800 at the time of activation, and/or a program depending on the hardware of the computer 800. The input/output chip 800-40 can also connect various input/output units via a parallel port, a serial port, a keyboard port, a mouse port, and the like to the input/output controller 800-20.

A program is provided by computer readable media such as the DVD-ROM 800-01 or the IC card. The program is read from the computer readable media, installed into the hard disk drive 800-24, RAM 800-14, or ROM 800-30, which are also examples of computer readable media, and executed by the CPU 800-12. The information processing described in these programs is read into the computer 800, resulting in cooperation between a program and the above-mentioned various types of hardware resources. An apparatus or method can be constituted by realizing the operation or processing of information in accordance with the usage of the computer 800.

For example, when communication is performed between the computer 800 and an external device, the CPU 800-12 can execute a communication program loaded onto the RAM 800-14 to instruct communication processing to the communication interface 800-22, based on the processing described in the communication program. The communication interface 800-22, under control of the CPU 800-12, reads transmission data stored on a transmission buffering region provided in a recording medium such as the RAM 800-14, the hard disk drive 800-24, the DVD-ROM 800-01, or the IC card, and transmits the read transmission data to network 800-50 or writes reception data received from network 800-50 to a reception buffering region or the like provided on the recording medium.

In addition, the CPU 800-12 can cause all or a necessary portion of a file or a database to be read into the RAM 800-14, the file or the database having been stored in an external recording medium such as the hard disk drive 800-24, the DVD-ROM drive 800-26 (DVD-ROM 800-01), the IC card, etc., and perform various types of processing on the data on the RAM 800-14. The CPU 800-12 can then write back the processed data to the external recording medium.

Various types of information, such as various types of programs, data, tables, and databases, can be stored in the recording medium to undergo information processing. The CPU 800-12 can perform various types of processing on the data read from the RAM 800-14, which includes various types of operations, processing of information, condition judging, conditional branch, unconditional branch, search/replace of information, etc., as described throughout this disclosure and designated by an instruction sequence of programs, and writes the result back to the RAM 800-14.

In addition, the CPU 800-12 can search for information in a file, a database, etc., in the recording medium. For example, when a plurality of entries, each having an attribute value of a first attribute is associated with an attribute value of a second attribute, are stored in the recording medium, the CPU 800-12 can search for an entry matching the condition whose attribute value of the first attribute is designated, from among the plurality of entries, and reads the attribute value of the second attribute stored in the entry, thereby obtaining the attribute value of the second attribute associated with the first attribute satisfying the determined condition.

The above-explained program or software modules can be stored in the computer readable media on or near the computer 800. In addition, a recording medium such as a hard disk or a RAM provided in a server system connected to a dedicated communication network or the Internet can be used as the computer readable media, thereby providing the program to the computer 800 via the network.

The present invention may be a system, a method, and/or a computer program product. The computer program product may include a computer readable storage medium (or media) having computer readable program instructions thereon for causing a processor to carry out aspects of the present invention. The apparatus of the embodiments of the present invention may include the computer readable medium and the processor or programmable circuitry operable to execute the instructions.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to individualize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

As made clear from the above, the embodiments of the present invention enable efficient generation of molecular structures.

What is claimed is:

1. A computer-implemented method, comprising:
   selecting, by a device operatively coupled to a processor, a vertex in an existing graph of a molecular structure;
   replacing, by the device, the selected vertex with a sub-structure representation of a molecule, the sub-structure representation including two or more vertices;
   connecting, by the device, a new vertex to the sub-structure representation in the existing graph to generate a new graph;
   labeling, by the device, each of a plurality of vertices of the new graph by a canonical labeling method; and
   determining, by the device, whether a vertex that has a minimum label is the new vertex.

2. The computer-implemented method of claim 1, wherein the canonical labeling method includes isomorphic-free exhaustive generation.

3. The computer-implemented method of claim 1, further comprising:
   abandoning, by the device, the new graph in response to determining that the vertex that has the minimum label is not the new vertex.

4. The computer-implemented method of claim 1, wherein the replacing the selected vertex includes:
   removing, by the device, the selected vertex from the existing graph; and
   connecting, by the device, the sub-structure representation of a molecule to a portion of a remaining graph at one of the two or more vertices in the sub-structure representation according to a type of the selected vertex.

5. The computer-implemented method of claim 1, wherein the sub-structure representation is an isomorphic equivalent representation of a sub-structure of the molecule.

6. The computer-implemented method of claim 1, wherein the sub-structure representation is an original representation of a sub-structure of the molecule.

7. The computer-implemented method of claim 1, wherein the new vertex represents a sub-structure of a molecule, and will be replaced with the sub-structure representation of the molecule.

8. The computer-implemented method of claim 1, wherein automorphisms of the labeling comprises a permutation group, wherein the method further comprises:
   before selecting the vertex in the existing graph, generating, by the device, an orbit of the permutation group including equivalent vertices in the existing graph in terms of labeling.

9. The computer-implemented method of claim 8, wherein the selecting the vertex in the existing graph includes:
   selecting, by the device, a single vertex among two or more equivalent vertices for each group of the plurality of groups in the orbit.

10. The computer-implemented method of claim 1, further comprising:
    determining, by the device, whether the new graph meets a determined requirement of the molecular structures; and
    abandoning, by the device, the new graph in response to determining that the new graph does not meet the determined requirement.

11. The computer-implemented method of claim 10, wherein the determined requirement includes at least one of a number of specific atoms or a number of specific fragments of molecular structures.

12. An apparatus comprising:
    a memory that stores computer executable components;
    a processing unit that executes the computer executable components stored in the memory, wherein the computer executable components comprise:
       at least one computer-executable component that:
          selects a vertex in an existing graph of a molecular structure;
          replaces the selected vertex with a sub-structure representation of a molecule, the sub-structure representation including two or more vertices;
          connects a new vertex to the sub-structure representation in the existing graph to generate a new graph;
          labels each of a plurality of vertices of the new graph by a canonical labeling method; and
          determines whether a vertex that has a minimum label is the new vertex.

13. The apparatus of claim 12, wherein the canonical labeling method includes isomorphic-free exhaustive generation.

14. The apparatus of claim 12, wherein the at least one computer-executable component also:
    abandons the new graph in response to a determination of that the vertex that has the minimum label is not the new vertex.

15. The apparatus of claim 12, wherein the replacement of the selected vertex includes:
    connection of the sub-structure representation of a molecule to a portion of the existing graph except the selected vertex to one of the two or more vertices in the sub-structure representation according to a type of the selected vertex.

16. The apparatus of claim 12, wherein the sub-structure representation is an isomorphic equivalent representation of a sub-structure of the molecule.

17. The apparatus of claim 12, wherein the sub-structure representation is an original representation of a sub-structure of the molecule.

18. The apparatus of claim 12, wherein the new vertex represents a sub-structure of a molecule, and will be replaced with the sub-structure representation of the molecule.

19. A computer program product facilitating molecular structure generation with substructure representations, the computer program product comprising a computer readable storage medium having program instructions embodied therewith, the program instructions executable by a processor to cause the processor to:
    select, by the processor, a vertex in an existing graph of a molecular structure;
    replace, by the processor, the selected vertex with a sub-structure representation of a molecule, the sub-structure representation including two or more vertices;

connect, by the processor, a new vertex to the sub-structure representation in the existing graph to generate a new graph;

label, by the processor, each of a plurality of vertices of the new graph by a canonical labeling method; and determine, by the processor, whether a vertex that has a minimum label is the new vertex.

20. The computer program product of claim 19, wherein the canonical labeling method includes isomorphic-free exhaustive generation.

21. The computer program product of claim 19, wherein the program instructions further cause the processor to:

abandon the new graph in response to determining that the vertex that has the minimum label is not the new vertex.

22. The computer program product of claim 19, wherein the replacement of the selected vertex includes:

connection of the sub-structure representation of a molecule to a portion of the existing graph except the selected vertex to one of the two or more vertices in the sub-structure representation according to a type of the selected vertex.

23. The computer program product of claim 19, wherein the sub-structure representation is an isomorphic equivalent representation of a sub-structure of the molecule.

24. The computer program product of claim 19, wherein the sub-structure representation is an original representation of a sub-structure of the molecule.

25. The computer program product of claim 19, wherein the new vertex represents a sub-structure of a molecule, and will be replaced with the sub-structure representation of the molecule.

* * * * *